(12) United States Patent
Liu (10) Patent No.: US 10,716,952 B2
(45) Date of Patent: Jul. 21, 2020

(54) FOCUSED RADIOTHERAPY APPARATUS AND RADIOTHERAPY EQUIPMENT THEREOF

(71) Applicant: CYBERMED RADIOTHERAPY TECHNOLOGIES CO., LTD., Xi'an (CN)

(72) Inventor: Haifeng Liu, Xi'an (CN)

(73) Assignee: OUR UNITED CORPORATION, Xi'an (CN)

( * ) Notice: Subject to any disclaimer, the term of this patent is extended or adjusted under 35 U.S.C. 154(b) by 139 days.

(21) Appl. No.: 15/749,784

(22) PCT Filed: Aug. 4, 2015

(86) PCT No.: PCT/CN2015/086026
§ 371 (c)(1),
(2) Date: Feb. 2, 2018

(87) PCT Pub. No.: WO2017/020244
PCT Pub. Date: Feb. 9, 2017

(65) Prior Publication Data
US 2019/0001146 A1   Jan. 3, 2019

(51) Int. Cl.
| | | |
|---|---|---|
| *A61N 5/10* | (2006.01) | |
| *A61N 5/01* | (2006.01) | |
| *A61B 6/00* | (2006.01) | |
| *A61B 6/04* | (2006.01) | |
| *A61B 6/03* | (2006.01) | |

(52) U.S. Cl.
CPC ............. *A61N 5/01* (2013.01); *A61N 5/1042* (2013.01); *A61N 5/1081* (2013.01); *A61B 6/032* (2013.01); *A61B 6/0457* (2013.01); *A61B 6/4007* (2013.01); *A61B 6/4429* (2013.01); *A61B 6/4441* (2013.01); *A61N 2005/1095* (2013.01)

(58) Field of Classification Search
CPC ..... A61B 6/032; A61B 6/0457; A61B 6/4007; A61B 6/4429; A61B 6/4441; A61B 5/01; A61B 5/1042; A61B 5/1081; A61B 2005/1095; A61N 5/01; A61N 5/1042; A61N 5/1081; A61N 2005/1095
See application file for complete search history.

(56) References Cited

U.S. PATENT DOCUMENTS

| | | |
|---|---|---|
| 5,627,870 A | 5/1997 | Kopecky |
| 2004/0184577 A1 | 9/2004 | Carlsson et al. |

(Continued)

FOREIGN PATENT DOCUMENTS

| | | |
|---|---|---|
| CN | 1666301 | 9/2005 |
| CN | 2736014 | 10/2005 |

(Continued)

*Primary Examiner* — Mark R Gaworecki
(74) *Attorney, Agent, or Firm* — Hemisphere Law, PLLC; Zhigang Ma (57) ABSTRACT

The present invention provides a focused radiotherapy apparatus comprising: at least one source part, provided with a plurality of radioactive sources arranged thereon; at least one collimation part enclosing the source part, and comprising a plurality of collimators aligned corresponding to the radioactive sources, the radiation rays emitted by the plurality of radioactive sources passing through the collimators and then converging to a focal point for treatment.

18 Claims, 6 Drawing Sheets

(56) References Cited

U.S. PATENT DOCUMENTS

| | | | | |
|---|---|---|---|---|
| 2010/0272240 A1* | 10/2010 | Cochrane | ............... | G01N 23/04 |
| | | | | 378/167 |
| 2014/0046212 A1* | 2/2014 | Deutschmann | .......... | A61B 6/03 |
| | | | | 600/567 |
| 2015/0202465 A1 | 7/2015 | Zhao | | |

FOREIGN PATENT DOCUMENTS

| | | | | |
|---|---|---|---|---|
| CN | 101195058 | | 6/2008 | |
| CN | 100512906 | | 7/2009 | |
| CN | 102441238 | | 5/2012 | |
| CN | 203408368 | | 1/2014 | |
| CN | 203647890 | | 6/2014 | |
| EP | 1057499 | A2 * | 12/2000 | .......... A61N 5/1081 |
| WO | 1994028973 | | 12/1994 | |
| WO | 2014166040 | | 10/2014 | |
| WO | 2015062093 | | 5/2015 | |
| WO | 2015096572 | | 7/2015 | |

* cited by examiner

FOCUSED RADIOTHERAPY APPARATUS AND RADIOTHERAPY EQUIPMENT THEREOF

TECHNICAL FIELD

The present invention relates to a radiation medical device, and more particularly to a focused radiotherapy apparatus and a radiotherapy equipment employing the focused radiotherapy apparatus.

BACKGROUND

In the radiotherapy industry, the technology of using Go-60 for focused radiotherapy is quite well developed. However, due to the intense radiation of Go-60 radioactive sources, a very thick and heavy shielding structure should be set up to a radiotherapy equipment, to prevent radiation leakage. Moreover, a traditional focused treatment head, which is part of the radiotherapy equipment, generally adopts the structure of shielding part, source part and collimation part sequentially arranged from the outside to the inside, so that the structure of the focused treatment head is very complicated and bulky. In addition, the focused treatment head usually requires as many collimator combinations as possible to obtain more collimation aperture combinations to meet different field sizes and dose requirements. However, regardless of rotatable collimation structure or translational collimation structure, the number of collimators that can be selected is limited due to the treatment space limitations, which greatly reduces the flexibility for the focused treatment head in clinical use.

SUMMARY

In order to solve the above technical problem, the present invention provides a focused radiotherapy apparatus and a radiotherapy equipment employing the focused radiotherapy.

An embodiment of the present invention provides a focused radiotherapy apparatus, which comprises: a source part provided with a plurality of radioactive sources; a pre-collimation part fixedly connected to the source part, the pre-collimation part comprising a plurality of pre-collimation holes, the pre-collimation holes being arranged corresponding to the radioactive sources one by one; a collimation part enclosing the source part and the pre-collimation, and is rotatable with respect to the source part and the pre-collimation, the collimation part comprising at least one curved surface on which a plurality of sets of collimators and/or shielding means in different sizes arranged corresponding to the radioactive sources, wherein the collimation part is configured to switch the positions between different groups of collimators and/or shielding means and the radioactive sources, to achieve different field sizes and/or shield at least part of the radiation beams from the source part; and a switch part being disposed outside the collimation part and movable relative to the source part, the pre-collimating part and the collimation part, so that the radiation beams of the radioactive sources can be focused or shielded.

Another embodiment of the present invention provides a radiotherapy equipment, which comprises a focused radiotherapy apparatus comprising a rotatable gantry, a treatment couch, and at least one focused radiotherapy apparatus according to any one of the claims 1 to 8, the focused radiotherapy apparatus being fixedly disposed on the gantry, radiation beams of the focused radiotherapy apparatus being focused to the couch.

For the focused radiotherapy and the radiotherapy equipment of the present invention, the collimation part is provided with at least one curved surface which is configured to receive collimators in different sizes, and the collimation part encloses the source part therein and is capable of being rotatable or movable relative to the source part. When the collimators are driven to be aligned with the radioactive sources in different positions, the combination of collimation can be greatly increased and the flexibility of formulating treatment plans for the patients is enhanced.

DETAILED DESCRIPTION

In order to make the objectives, technical solutions and advantages of the present invention more comprehensible, the present invention is further described in detail below with reference to the accompanying drawings and embodiments. It should be understood that the specific embodiments described herein are merely used to explain the present invention, and are not intended to limit the present invention.

Figure 1:
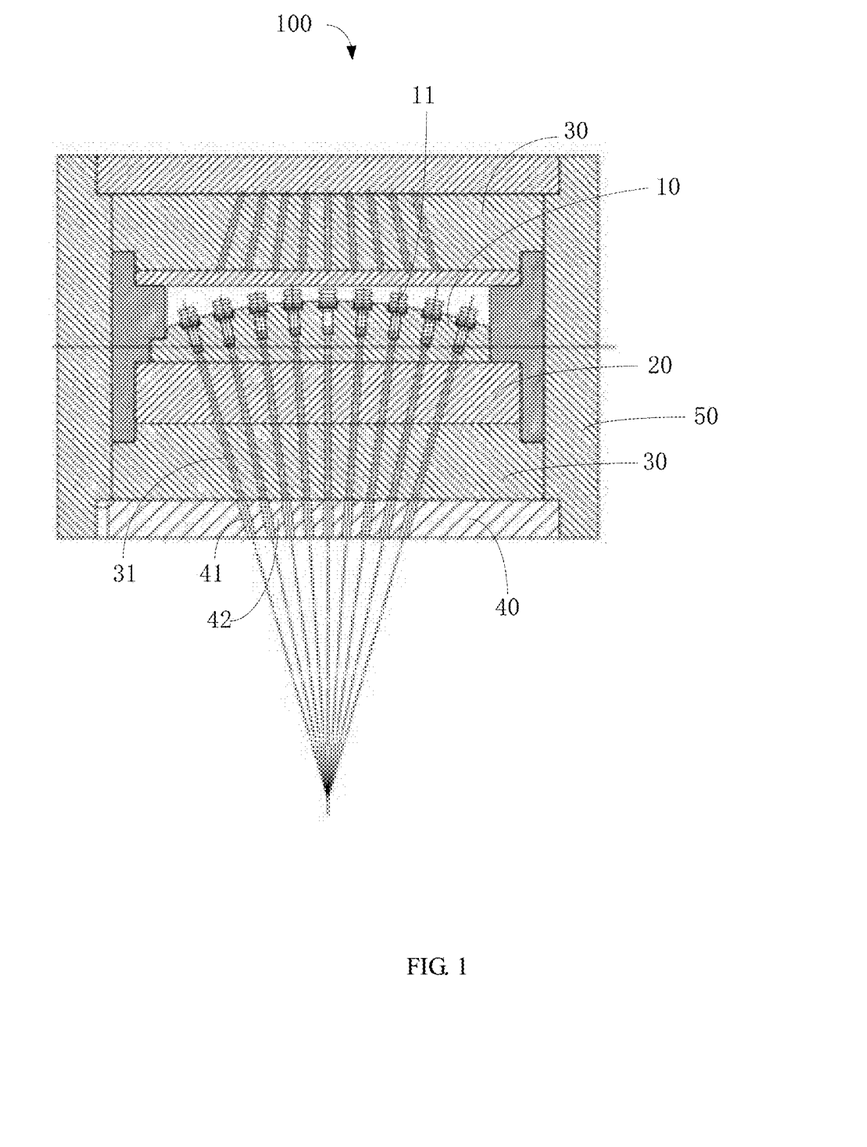
FIG. 1 is a schematic cross-sectional view taken along an axial direction of a focused radiotherapy apparatus which is in a turn-on state, according to an embodiment of the present invention.
Figure 2:
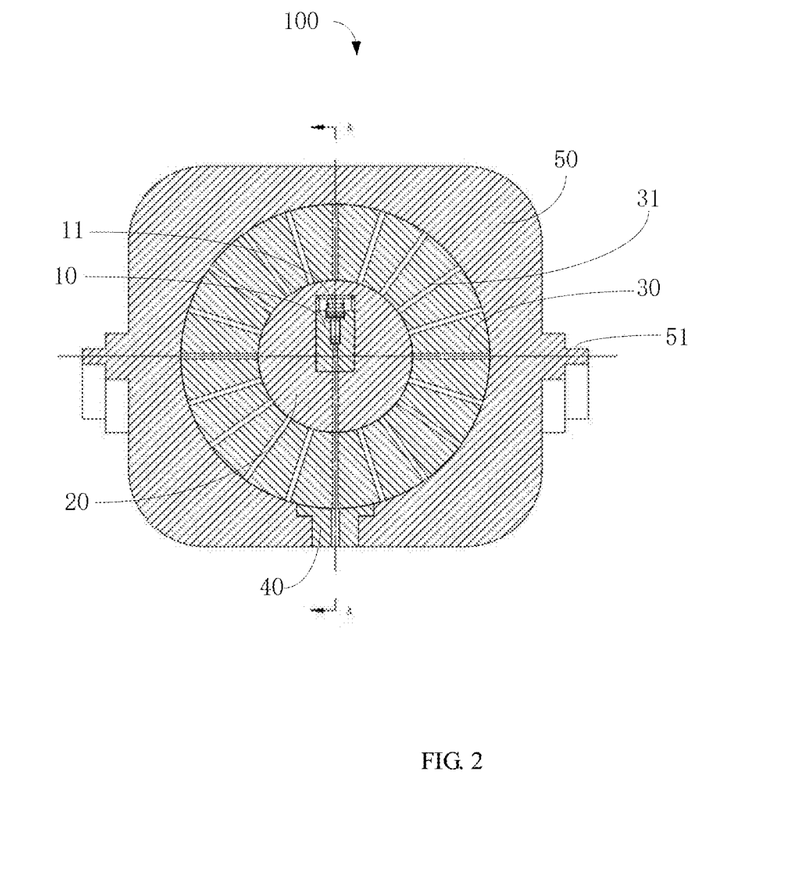
FIG. 2 is a schematic cross-sectional view taken along a radial direction of the focused radiotherapy apparatus of FIG. 1.
Figure 3:
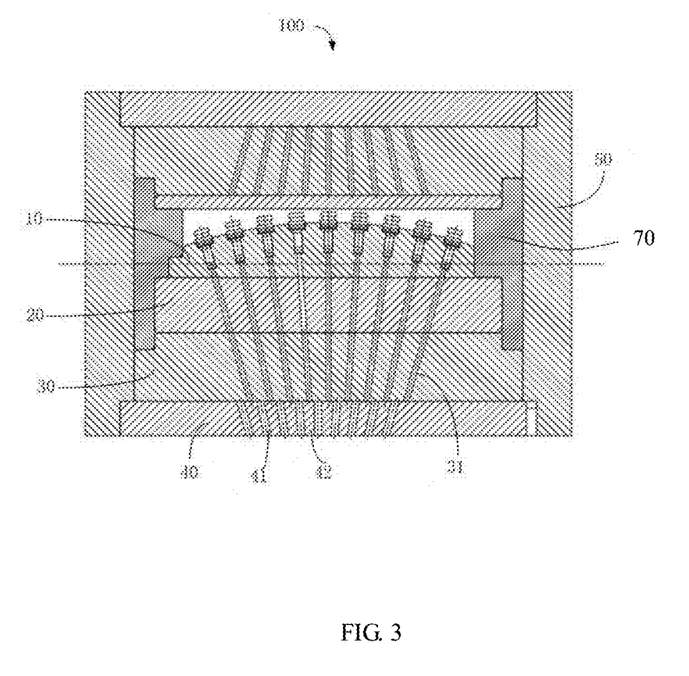
FIG. 3 is a cross-sectional schematic view taken along the axial direction of the focused radiotherapy apparatus of FIG. 1 which is in a turn-off state.

Referring to FIGS. 1 to 3, the present disclosure provides a focused radiotherapy apparatus 100, which includes a source part 10, a pre-collimation part 20, a collimation part 30 and a switch part 40, at least. The source part 10 is fixedly connected to the pre-collimation part 20. The collimation part 30 covers or encloses the source part 10 and the pre-collimation part 20. The switch part 40 is disposed outside the collimation part 30 and is movable/rotatable relative to the collimation part 30.

Specifically, at least one row of radioactive sources 11 are disposed on the source part 10. In this embodiment, the source part 10 is formed with an arc surface, and the radioactive sources 11 are arranged in a matrix on the arc surface of the source part 10. It is understood that, in other embodiments, the source part 10 may be arranged with more than one row of radioactive sources 11, e.g. as required to form a conical arrangement, and ensure that all the radioactive sources 11 can focus the beams to a focal point. In this embodiment but not for limitation, the radioactive source 11 is made of Co-60.

The pre-collimation part 20 is fixedly connected to the source part 10 by screwing or the like. The pre-collimation part 20 includes a plurality of pre-collimation holes, and the pre-collimation holes correspond to the radioactive sources 11 in a one-to-one manner, to preliminarily collimate the radiation beams. In this embodiment, the source part 10 and the pre-collimation part 20 are connected to the collimation part 30 through bearings 70 fixed on two ends of the collimation part 30.

Figure 4:
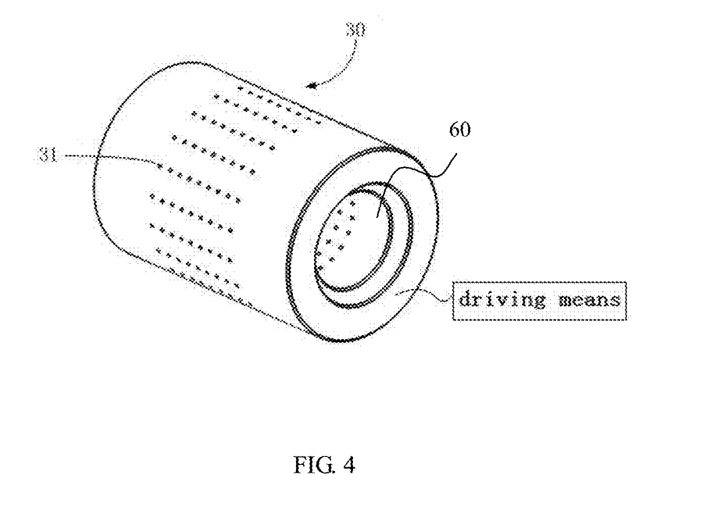
FIG. 4 is a schematic structural diagram of a collimation part of the focused radiotherapy apparatus, according to an embodiment of the present invention.

With reference to FIG. 4, the collimation part 30 is disposed rotatably relative to the source part 10 and the pre-collimation part 20. The collimation part 30 includes at least one arc-shaped curved surface. A plurality groups of collimators and/or shielding means 31 in different sizes are arranged on the curved surface. Each group of collimators and/or shielding means 31 are arranged corresponding to the radioactive sources 11. By rotating the collimation part 30, different sets of collimators and/or shielding means 31 are switched to be aligned with the radioactive sources 11, to achieve different field sizes and perform shielding for at least part of the radioactive sources. In an embodiment, the collimation part 30 is shaped as a cylinder, and a plurality sets of the collimators/shielding means 31 are disposed on the cylinder wall along the axial direction thereof, corresponding to the radioactive sources 11 on the source part 10. The source part 10 and the pre-collimation part 20 are received in a cavity formed by the collimation part 30.

Figure 5:
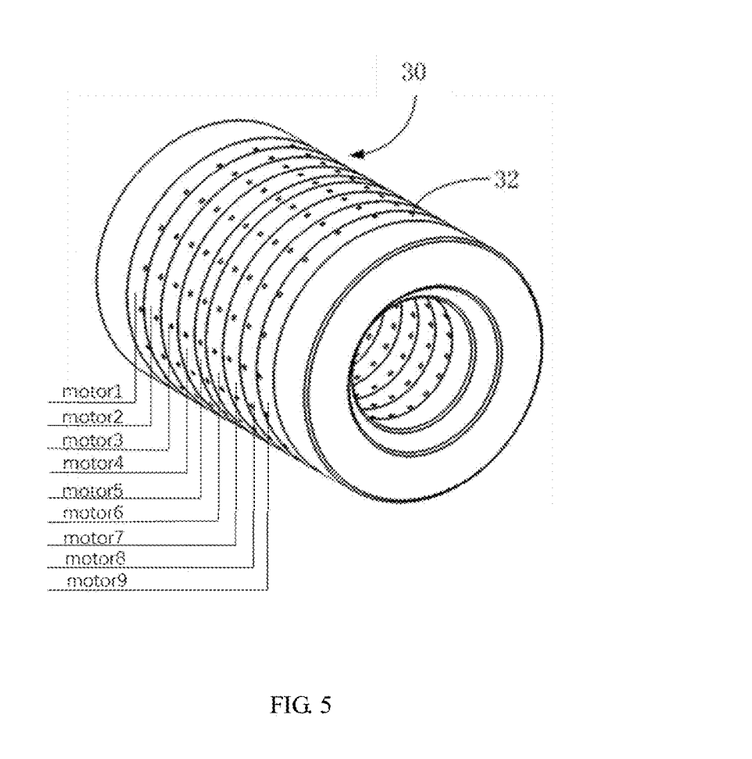
FIG. 5 is a schematic structural diagram of a collimation part of the focused radiotherapy apparatus, according to another embodiment of the present invention.

Referring to FIG. 5, in another embodiment, the collimation part 30 is still shaped as a cylinder, but may be assembled with a plurality of annular rings 32 sequentially spliced along the axial direction thereof. Each annular ring 32 may be movable independently, and corresponds to one or more radioactive sources 11. The collimators set on each of two rings 32 have the same or different sizes. In this way, more collimator combinations are available. Taking eight radioactive sources 11 to be employed as an example, if each radioactive source 11 is arranged in correspondence with an independently movable collimator ring, as described above, and each annular ring 32 is arranged with 15 collimators, there would be $15^8=2562890625$ collimation options. In a use, when the collimation part 30 is moved or rotated to a specific position, a group of collimators 31 on the collimation part 30 can be aligned corresponding to the radioactive sources 11 in a one-to-one manner, so that the radiation beams of the radioactive sources 11 can pass through the collimators and further pass through the switch part 40, to form a first dose field. When the collimation part 30 is moved or rotated to another specific position, for example, after 180 degrees of rotation, the mentioned group of collimators 31 deviates from the radioactive sources 11 and in a standby state, while another group of collimators 31 with different sizes are aligned with the radioactive sources 11, and the radiation beams from the radioactive sources 11 form a second dose field after passing through the switch part 40. With such a structure, not only more and more collimation combinations can be provided, but the collimators in standby state can be placed above the source part 10, and additional space can be saved while increasing the number of collimation combinations.

It can be understood that, in other embodiments, the collimation part 30 may be structured with other shapes, for example, with a plurality of curved surfaces which are axially spliced, and each of the curved surfaces is provided with collimators and shielding means with different apertures. Alternatively, the collimation part 30 may include only two curved surfaces opposite to each other, but still be shaped as a cylinder.

The switch part 40 is disposed outside the collimation part 30 and corresponding to the emitting direction of the radioactive source 11. The switch part 40 is movable relative to the source part 10, the pre-collimation part 20 and the collimation part 30, respectively, to quickly turn on and/or shield the radioactive sources 11, so that the radiation beams of the radioactive sources 11 can be focused or shielded. Specifically, the switch part 40 is provided with a plurality of through holes 41 and shielding rods 42. When the switch part 40 is moved to a first state (e.g., the turn-on state), the through holes 41 on the switch part 40 are aligned with the collimators of the collimation part 30, so that the radiation beams/rays of the radioactive source 11 can pass through the switch part 40 to be focused. When the switch part 40 is moved to a second state (e.g., the turn-off state), the shielding rod 42 on the switch part 40 is aligned with the collimator of the collimation part 30 to shield the rays. In addition to ensuring that the radioactive source 11 is shielded during in the turn-off state, the switching part 40 is also capable of rapid turning-on and shielding of the source part 10 in accordance with the treatment plan or quickly shielding the source part 10 in the event of an accident during treatment.

In this embodiment, the focused radiotherapy apparatus 100 further includes a shielding shell 50, which encloses the collimation part 30. And, the collimation part 30 is rotatable relative to the shielding shell 50. In this embodiment, the collimation part 30 is connected to the inner wall of the shielding shell 50 through bearings (not shown). Furthermore, the shielding shell 50 defines an opening (not labeled) for receiving the switch part 40, so that the radiation beams of the radioactive sources 11 can exit the shielding shell 50 therethrough. In addition, the shielding shell 50 is a supporting part and a shielding part of the whole focused radiotherapy apparatus 100. The external shape of the shielding shell 50 can be specially designed according to equipment requirements, functional requirements and the like, so as to adapt to different equipment racks and achieve better treatment effect. In this embodiment, at least one groove 51 is designed on the shielding shell 50 for mounting at least one arc-shaped guide rail (not shown). The focused radiotherapy apparatus 100 can be connected to a gantry through the arc-shaped guide rail, so that the focused radiotherapy apparatus 100 can swing in an axial direction of the gantry and then change the incidence angle of the radiation beams.

In order to drive the collimation part 30 to move or rotate, in the embodiment, the focused radiotherapy apparatus 100 further includes a driving means 60, configured for driving the collimation part 30 to rotate according to a treatment plan. As such, the preset collimators and/or shielding means are aligned with the radioactive sources, therefore the switching of the collimator and shielding means can be achieved. In another embodiment, when the collimation part 30 is constituted with the plurality of annular rings 32, the driving means 60 includes a plurality of motors correspondingly connected to the annular rings 32, and the driving means 60 is configured to control the motors according to the treatment plan, respectively, to drive each annular ring 32 of the collimation part 30 to rotate to preset positions.

In the focused radiotherapy apparatus 100 of the present invention, the collimation part 30 is provided with at least one curved surface, and the collimation part 30 encloses the source part 10 therein and can rotate with respect to the source part 10. When different collimators are disposed on the collimation part 30, the number of collimation combination can be greatly increased, and the flexibility of the treatment plans can be developed.

Figure 6:
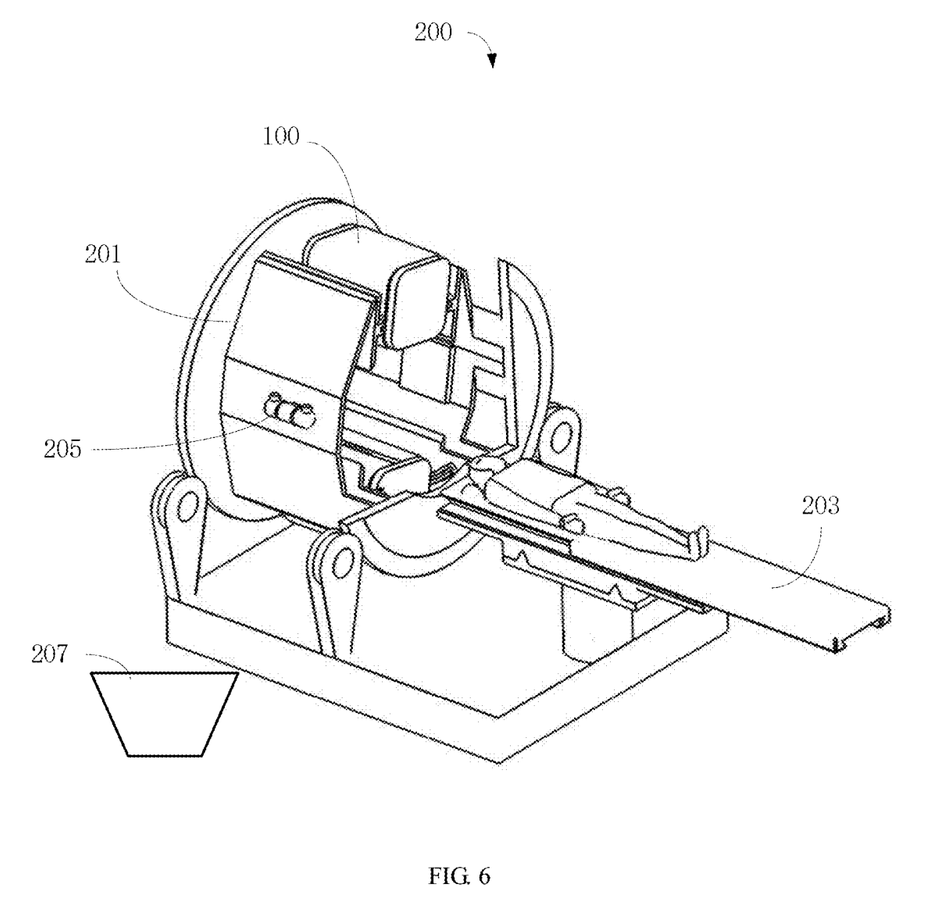
FIG. 6 is a schematic structural view of a radiotherapy equipment employing the focused radiotherapy apparatus of FIG. 1, according to an embodiment of the present invention.

Referring to FIG. 6, the present invention further provides a radiotherapy equipment 200 that employs the above-mentioned focused radiotherapy apparatus 100. More specifically, the radiotherapy equipment 200 includes a rotatable gantry 201, a treatment couch 203, at least one focused radiotherapy apparatus 100 mentioned above and an image guidance system 205. The gantry 201 is rotatable or not. The focused radiotherapy apparatus 100 is disposed on the gantry 201. The radiation emitted from the focused radiotherapy apparatus 100 is focused to a specific position, which is located in correspondence to a patient's lesion. It is understood that the patient's position can be adjusted by moving the treatment couch 203. The image guidance system 205 is disposed on the gantry 201 for acquiring a lesion image at a focus point and processing the image by a backend processor. In this embodiment, the image guidance system 205 is a CBCT (cone beam computed tomography) system, and the treatment couch 203 is a six-dimensional bed which can be movable in six directions.

When the number of focused radiotherapy apparatus 100 on the gantry 201 is increased, the collimation combinations will be increased in order of magnitude. Taking two focused radiotherapy apparatus 100 to be employed as an example, and assuming that fifteen (which can be more) groups of collimators in different size are disposed on the collimation part 30. In this condition, even if using the cylindrical collimation part 30 (i.e. the collimation part 30 which is not constituted with the plurality of independent annular rings 31 but formed as a cylinder in an integration, as mentioned above), there will be 15²=225 kinds of collimation options, which are basically to meet the requirements of clinical use.

In addition, the radiotherapy equipment 200 may further include a storage box 207 disposed beside the treatment couch 203 for storing the source part 10, when the focused radiotherapy apparatus 100 is not in operation. Since Go-60 is particularly radioactive, it is particularly important for its protection. Placing the source part 10 in the dedicated storage box 207 when in a non-operation state, will reduce the shielding requirements for the room and equipment while ensuring safety. Of course, when the device itself and the surrounding environment is well-shielded, a separate storage device may not be used.

As the gantry 201, CBCT system, six-dimensional bed and other components already have mature technology, it is not repeated here.

In conclusion, for the focused radiotherapy 100 and the radiotherapy equipment 200 of the present invention, the collimation part 30 is provided with at least one curved surface which is configured to receive collimators 30 in different sizes, and the collimation part 30 encloses the source part 10 therein and is capable of being rotatable or movable relative to the source part 10. When the collimators 30 are driven to be aligned with the radioactive sources 11 in different positions, the combination of collimation can be greatly increased and the flexibility of formulating treatment plans for the patients is enhanced. In addition, the structure of the focused radiotherapy apparatus 100 will not be more complicated while increasing the number of collimator or collimation combinations.

The foregoing descriptions are merely preferred embodiments of the present invention, and are not used to limit the present invention. Any modifications, equivalent replacements and improvements made within the spirit and principle of the present invention should be within the scope.

I claim:

1. A focused radiotherapy apparatus, comprising:
   a source part provided with a plurality of radioactive sources;
   a pre-collimation part being fixedly connected to the source part, and comprising a plurality of pre-collimation holes arranged corresponding to the radioactive sources one by one;
   a collimation part enclosing the source part and the pre-collimation, wherein the collimation part is rotatable with respect to the source part and the pre-collimation part, and the collimation part comprises at least one curved surface on which a plurality of sets of collimators and/or shielding means in different sizes arranged corresponding to the radioactive sources, the collimation part is configured to switch the positions between different groups of collimators and/or shielding means and the radioactive sources, to achieve different field sizes and/or shield at least part of the radiation beams from the source part; and
   a switch part being disposed outside the collimation part and movable relative to the source part, the pre-collimating part and the collimation part, so that the radiation beams of the radioactive sources be focused or shielded.

2. The focused radiotherapy apparatus according to claim 1, wherein the collimation part is shaped as a cylinder, the plurality of collimators and/or shielding means are provided on the cylinder wall corresponding to the source part along an axial direction thereof, the source part and the pre-collimation part are received in a cavity formed by the collimation part.

3. The focused radiotherapy apparatus according to claim 1, wherein the collimation part is in a cylindrical shape and comprises a plurality of annular rings sequentially aligned in an axial direction thereof, and each of the annular rings is rotatable independently and corresponds to one or more radioactive sources, and the collimators provided on each two rings have the same or different sizes.

4. A focused radiotherapy apparatus comprising:
   at least one source part, provided with a plurality of radioactive sources arranged thereon;
   at least one collimation part enclosing the source part, and comprising a plurality of collimators aligned corresponding to the radioactive sources, the radiation rays emitted by the plurality of radioactive sources passing through the collimators and then converging to a focal point for treatment; and
   a shielding shell enclosing the collimation part, and the collimation part is rotatable relative to the shielding shell.

5. The focused radiotherapy apparatus according to claim 4, wherein a plurality of groups of collimators with different sizes are arranged on the collimation part, and the collimation part is rotatable relative to the source part.

6. The focused radiotherapy apparatus according to claim 5, wherein the collimation part is provided with at least one shielding means for at least partially shielding the radiation from the radioactive sources.

7. The focused radiotherapy apparatus according to claim 4, wherein the collimation part is shaped as a cylinder, and the focused radiotherapy apparatus further comprises a driving means for driving the collimation part to rotate.

8. The focused radiotherapy apparatus according to claim 7, wherein the collimation part comprises a plurality of annular rings sequentially spliced in the axial direction thereof, the annular ring is provided with collimators, and each annular ring is rotatable relative to the source part, independently.

9. The focused radiotherapy apparatus according to claim 8, wherein each of the annular rings corresponds to one or more of the radioactive sources.

10. The focused radiotherapy apparatus according to claim 9, wherein the collimators provided on each of the annular rings are in the same or different sizes.

11. The focused radiotherapy apparatus according to claim 8, wherein the driving means comprises a plurality of motors correspondingly coupled to the plurality of annular rings, and the driving means is configured to respectively control the plurality of motors according to a treatment plan, for driving the plurality of annular rings to rotate.

12. The focused radiotherapy apparatus according to claim 4, further comprising a pre-alignment part on which a plurality of pre-alignment holes is disposed corresponding to the plurality of radioactive sources, wherein the pre-alignment part is fixedly connected to the source part, and the collimation part encloses the source part and the pre-alignment part.

13. The focused radiotherapy apparatus according to claim 12, wherein the source part and the pre-alignment part are connected to the collimation part by bearings, and the bearings are fixed on both ends of the collimation part.

14. The focused radiotherapy apparatus according to claim 4, further comprising a switch part provided with at least one through hole and at least one shielding rod, wherein the switch part is disposed outside the collimation part and movable relative to the collimation part, so that the rays emitted by the plurality of radioactive sources pass through the through holes or are shielded by the shielding rod.

15. A radiotherapy equipment, comprising at least one focused radiotherapy apparatus comprising:
 at least one source part, provided with a plurality of radioactive sources arranged thereon;
 at least one collimation part enclosing the source part, and comprising a plurality of collimators aligned correspondingly to the radioactive sources, the radiation rays emitted by the plurality of radioactive sources passing through the collimators and then converging to a focal point for treatment; and
 a shielding shell enclosing the collimation part, and the collimation part is rotatable relative to the shielding shell.

16. The radiotherapy equipment according to claim 15, further comprising a gantry, wherein the focused radiotherapy apparatus is mounted on the gantry.

17. The radiotherapy equipment according to claim 15, further comprising an image guidance system mounted on the gantry.

18. The radiotherapy equipment of claim 15, further comprising a storage box for storing the source part when the focused radiotherapy apparatus is not in operation.

\* \* \* \* \*